United States Patent
Dragna et al.

(10) Patent No.: US 10,845,346 B2
(45) Date of Patent: Nov. 24, 2020

(54) COMPOSITIONS, APPARATUS, AND METHODS FOR DETERMINING HARDNESS OF WATER AND MAGNESIUM ION IN AN ANALYTE COMPOSITION

(71) Applicant: Water Lens, LLC, Houston, TX (US)

(72) Inventors: Justin M. Dragna, Houston, TX (US);
Adam Garland, Houston, TX (US);
Tyler West, Houston, TX (US)

(73) Assignee: WATER LENS, LLC, Houston, TX (US)

( * ) Notice: Subject to any disclaimer, the term of this patent is extended or adjusted under 35 U.S.C. 154(b) by 141 days.

(21) Appl. No.: 15/577,793

(22) PCT Filed: May 26, 2016

(86) PCT No.: PCT/US2016/034371
§ 371 (c)(1),
(2) Date: Nov. 29, 2017

(87) PCT Pub. No.: WO2016/196207
PCT Pub. Date: Dec. 8, 2016

(65) Prior Publication Data
US 2018/0156763 A1 Jun. 7, 2018

Related U.S. Application Data

(60) Provisional application No. 62/168,554, filed on May 29, 2015, provisional application No. 62/168,543, filed on May 29, 2015.

(51) Int. Cl.
*G01N 31/00* (2006.01)
*G01N 31/22* (2006.01)
(Continued)

(52) U.S. Cl.
CPC ......... *G01N 31/22* (2013.01); *G01N 33/1813* (2013.01); *G01N 33/1853* (2013.01); *B01L 3/50855* (2013.01)

(58) Field of Classification Search
CPC ...................................................... G01N 31/22
(Continued)

(56) References Cited

U.S. PATENT DOCUMENTS

| | | |
|---|---|---|
| 4,902,621 A | 2/1990 | Witt |
| 5,114,974 A * | 5/1992 | Rubin ............. A61K 31/28 514/566 |

(Continued)

FOREIGN PATENT DOCUMENTS

| | | |
|---|---|---|
| RU | 2158179 | 10/2000 |
| WO | WO 1993/003100 | 2/1993 |
| WO | WO 2005/095638 | 10/2005 |

OTHER PUBLICATIONS

Search Report issued in International Application No. PCT/US2016/034371, dated Aug. 18, 2016.

*Primary Examiner* — Christine T Mui
*Assistant Examiner* — Emily R. Berkeley
(74) *Attorney, Agent, or Firm* — Norton Rose Fulbright US LLP

(57) ABSTRACT

Compositions, kits, and methods of using the kits and compositions to determine the hardness of and/or magnesium concentration in a solution are described. The kit can include a lyophilized composition that has an absorbance at a detectable wavelength in response to the hardness of the solution and or the concentration of magnesium in the solution.

18 Claims, 5 Drawing Sheets

(51) Int. Cl.
*G01N 33/18* (2006.01)
*B01L 3/00* (2006.01)

(58) Field of Classification Search
USPC .......................................................... 436/79
See application file for complete search history.

(56) References Cited

U.S. PATENT DOCUMENTS

| | | |
|---|---|---|
| 5,397,710 A | 3/1995 | Steinman |
| 2004/0033484 A1 | 2/2004 | Krenn et al. |
| 2005/0221414 A1* | 10/2005 | Varadi .................... G01N 33/86 435/23 |
| 2007/0144922 A1* | 6/2007 | Imoarai .................. G01N 33/52 206/204 |
| 2008/0076675 A1* | 3/2008 | Bjornvad ................. C12N 9/20 506/11 |

* cited by examiner

COMPOSITIONS, APPARATUS, AND METHODS FOR DETERMINING HARDNESS OF WATER AND MAGNESIUM ION IN AN ANALYTE COMPOSITION

CROSS REFERENCE TO RELATED APPLICATIONS

This application is a national phase under 35 U.S.C. § 371 of International Application No. PCT/US2016/034371, filed May 26, 2016, which claims the benefit of U.S. Provisional Application No. 62/168,543, filed on May 29, 2015 and U.S. Provisional Application No. 62/168,554, filed on May 29, 2015. The contents of each of the referenced applications are incorporated into the present application by reference.

BACKGROUND OF THE INVENTION

A. Field of the Invention

The invention generally concerns the determination of the hardness of a solution and the magnesium ion concentration of a solution. In particular, the kits and methods of the present invention are used to determine the hardness in an analyte composition and magnesium ion concentrate in an analyte composition by adding the analyte composition to a lyophilized composition in each microwell of the plurality of microwells to form a solution in each microwell having a detectable absorbance in response to the hardness or magnesium ion in the analyte composition.

B. Description of Related Art

The determination of hardness and the magnesium content of various aqueous liquids is important for many manufacturing and environmental purposes. For example, it is often necessary to know the hardness and/or amount of magnesium in wastewater, groundwater, food products, chemical processing fluids, oil well water or other natural or effluent liquid sources. Currently methods to test water hardness at remote sites include test strips or titration methods using visual indicators and methods to test magnesium concentration in water utilize complexometric titration and atomic absorption spectrometric procedures with only complexometric titration methods being practical for rapid water analysis and/or remote testing applications. Typically, "total hardness" and the relative concentrations of both magnesium and calcium in a water sample is accomplished by a titration method using the chelating agent, EDTA (ethylenediamine tetraacetic acid) and indicator, such as ERICHROME® Black T. The titration is conducted under conditions where both ions react with the EDTA, and the end point is detected after both are titrated to provide total hardness. For magnesium ion content, magnesium can be precipitated as magnesium hydroxide by increasing the pH. A subsequent titration of the solution determines only the remaining calcium ion, which remains soluble. The magnesium content can be determined by the difference. While potentially accurate with careful execution, this titration method suffers from many disadvantages and is time consuming. First, other metals found in water such as iron, aluminum, and manganese that also have affinities for EDTA can affect the measurement. Secondly, the visual technique requires the analyst to manually titrate the solutions and requires the subjective determination of a color change. These disadvantages often result in errors resulting from the analyst overshooting or misjudging the color change at the endpoint. Thus, in many cases the titration method must be repeated. Third, EDTA is considered an environmental pollutant.

SUMMARY OF THE INVENTION

A solution to the disadvantages of a visual titration method and the use of EDTA has been discovered. In particular, the solution for hardness resides in the use of colorimetric assay that includes lyophilized composition samples in a microwell plate. The compositions can include a colorimetric indicator that has an absorbance at a detectable wavelength in response to the hardness of the solution. For magnesium ion, the solution resides in the use of lyophilized compositions in a microwell plate. The compositions include a colorimetric indicator for magnesium. In some embodiments the solution for hardness and the solution for magnesium ion include lyophilized samples/compositions for both hardness and magnesium ion in the same microwell plate.

Analyte samples are added to the lyophilized samples/compositions and the absorbance of the resulting samples is measured and the hardness or magnesium concentration of the analyte composition is determined based on the measured absorbance value. Notably, the present invention eliminates the drawbacks of traditional manual titrations by eliminating the subjective naked-eye determination and provides a rapid analysis and accurate analysis of the analyte composition at the user site. The user simply has to add the analyte composition, or analyte solutions, to each microwell in the plate instead of manually titrating each analyte solutions. Furthermore, the present invention removes the subjective naked-eye determination of an endpoint by using a spectrophotometer. In addition, the present invention allows one to test both hardness and magnesium ion using the same microwell.

In one aspect of the invention, there is disclosed a composition for determining the hardness and/or magnesium content of a solution including an indicator, a buffer, and one or more excipients, wherein the composition has an absorbance at a detectable wavelength in response to hardness of and/or magnesium ion comprised in the solution. The indicator includes one or more of 3-hydroxy-4-(2-hydroxy-5-methylphenylazo)naphthalene-1-sulfonic acid (Calmagite), triethanol ammonium 3-hydroxy-4-(2-hydroxy-5-methylphenylazo)naphthalene-1-sulfonate (Calmagite triethanolammonium salt), 3-hydroxy-4-[(1-hydroxy-2-naphthyl)azo]naphthalene-1-sulphonate, sodium 3-hydroxy-4-[(1-hydroxy-2-naphthyl)azo]naphthalene-1-sulphonate (ERICHROME® Blue Black B), 2-hydroxy-1-(1-hydroxy-2-naphthyl azo)-6-nitronaphthalene-4-sulfonic acid, sodium 2-hydroxy-1-(1-hydroxy-2-naphthylazo)-6-nitronaphthalene-4-sulfonic acid (ERICHROME® Black T), sodium 4-hydroxy-3-[2-hydroxy-3-(2,4-dimethylphenylaminocarbonyl)-1-naphthylazobenzenesulfonate (Magonsulfonate), 4-(4-nitrophenylazo)-1-naphthol (Magneson II), with 3-hydroxy-4-(2-hydroxy-5-methylphenylazo)naphthalene-1-sulfonic acid (Calmagite) being preferred. The buffer includes one or more of N-cyclohexyl-3-aminopropanesulfonic acid (CAPS), camphor sulfonic acid (CSA), p-toluenesulfonic acid (PTSA), 1,4-piperazineethanesulfonic acid (PIPES), 4-(2-hydroxyethyl)-1-piperazineethanesulfonic acid (HEPES), 3-(N-morpholino)propanesulfonic acid (MOPS), and 2-(N-morpholino)ethanesulfonic acid (MES), with N-cyclohexyl-3-aminopropanesulfonic acid (CAPS) being preferred. The excipients include one or more of a polyethylene glycol, a 1,1,3,3-tetramethylbutyl)phenyl-polyethylene glycol, (2-hydroxyl propyl)-β-cyclodextrin, glycine, cellulose, citrate, lactose, mannitol, xylitol, sucrose, and polyvinylpyrrolidone, with polyethylene glycol (PEG 4000) and 1,1,3,3-tetramethylbutyl)phenyl-polyethylene glycol (TRITON™ X-100) being preferred.

In one aspect, a composition for determining the hardness of a solution further comprises a metal complexation ligand. The metal complexation ligand includes one of more of ethylenediaminetetraacetic acid disodium magnesium salt tetrahydrate ($Na_2MgEDTA$), ethylenediaminetetraacetic acid (EDTA), iminodisuccinic acid (IDS), polyaspartic acid, ethylenediamine-N,N'-disuccinic acid (EDDS), methylglycinediacetic acid (MGDA), L-glutamic acid N,N-diacetic acid (GLDA), 1,2-bis(o-aminophenoxy)ethane-N,N,N',N'-tetraacetic acid (BAPTA), and ethylene glycol tetraacetic acid (EGTA), with ethylenediaminetetraacetic acid disodium magnesium salt tetrahydrate ($Na_2MgEDTA$) being preferred.

The composition can be a powder. The powder can be made by providing an aqueous solution of the composition to one or more containers and subjecting at least one of the containers to lyophilizing conditions sufficient to remove the water from the aqueous solution to form the powder. In some instances, the one or more containers are microwells of a microwell plate. The powder can be packaged (for example, a bag, vial, or encapsulated). In some instances, a microwell plate contains powder composition for a hardness assay and contains powder composition for a magnesium ion assay.

In one aspect of the invention, there is disclosed a hardness and/or magnesium ion assay kit. The kit includes a) a microwell plate and b) a lyophilized composition including an indicator, a buffer, and one or more excipients. For the lyophilized composition in a hardness assay kit, the lyophilized composition further includes a metal complexation ligand. For a combined of kits or either kit, a plurality of microwells of the microwell plate contain the lyophilized composition such that when an analyte composition is added to the lyophilized composition in each microwell of the plurality of microwells a solution forms having an absorbance at a detectable wavelength in response to hardness and/or magnesium ion comprised in the analyte composition. By developing calibration curves based on these proportions, the hardness and/or magnesium concentration can be determined quantitatively. The detectable wavelength can be between 400 and 700 nm, between 600 and 670, and preferably at 650 nm. The microwell plate can include 6, 24, 96, 384, or 1536 microwells. In some aspects of the invention, the microwell plate includes 6 microwells and each microwell contains the same amount of composition or at least 2 microwells have the same amount of composition and the rest of the microwells have a different amount of composition. In other aspects of the invention, the microwell plate has at least 24 or 96 microwells and at least 10 microwells contain the same amount of composition solutions or at least 10 microwells contain the same amount of composition, and some of the microwells have a different amount of composition as other microwells. The indicator includes one or more of 3-hydroxy-4-(2-hydroxy-5-methylphenylazo)naphthalene-1-sulfonic acid (Calmagite), triethanol ammonium 3-hydroxy-4-(2-hydroxy-5-methylphenylazo)naphthalene-1-sulfonate (Calmagite triethanol ammonium salt), 3-hydroxy-4-[(1-hydroxy-2-naphthyl)azo]naphthalene-1-sulphonate, sodium 3-hydroxy-4-[(1-hydroxy-2-naphthyl)azo]naphthalene-1-sulphonate (ERICHROME® Blue Black B), 2-hydroxy-1-(1-hydroxy-2-naphthylazo)-6-nitronaphthalene-4-sulfonic acid, sodium 2-hydroxy-1-(1-hydroxy-2-naphthylazo)-6-nitronaphthalene-4-sulfonic acid (ERICHROME® Black T), sodium 4-hydroxy-3-[2-hydroxy-3-(2,4-dimethylphenylaminocarbonyl)-1-naphthylazobenzenesulfonate (Magonsulfonate), 4-(4-nitrophenylazo)-1-naphthol (Magneson II), with 3-hydroxy-4-(2-hydroxy-5-methylphenylazo)naphthalene-1-sulfonic acid (Calmagite) being preferred. The buffer includes one or more of N-cyclohexyl-3-aminopropanesulfonic acid (CAPS), camphor sulfonic acid (CSA), p-toluenesulfonic acid (PTSA), 1,4-piperazineethanesulfonic acid (PIPES), 4-(2-hydroxyethyl)-1-piperazineethanesulfonic acid (HEPES), 3-(N-morpholino)propanesulfonic acid (MOPS), and 2-(N-morpholino)ethanesulfonic acid (MIES), with N-cyclohexyl-3-aminopropanesulfonic acid (CAPS) being preferred. The excipients include one or more of a polyethylene glycol, a 1,1,3,3-tetramethylbutyl)phenyl-polyethylene glycol, (2-hydroxylpropyl)β-cyclodextrin, glycine, cellulose, citrate, lactose, mannitol, xylitol, sucrose, and polyvinylpyrrolidone, with polyethylene glycol (PEG 4000) and 1,1,3,3-tetramethylbutyl)phenyl-polyethylene glycol (TRITON™ X-100) being preferred. In a preferred aspect, the lyophilized composition includes essentially 3-hydroxy-4-(2-hydroxy-5-methylphenylazo)naphthalene-1-sulfonic acid (Calmagite), N-cyclohexyl-3-aminopropanesulfonic acid, PEG 3000, and TRITON™ X-100.

In one aspect, the metal complexation ligand in a kit for determining the hardness of a solution includes one of more of ethylenediaminetetraacetic acid disodium magnesium salt tetrahydrate ($Na_2MgEDTA$), ethylenediaminetetraacetic acid (EDTA), iminodisuccinic acid (IDS), polyaspartic acid, ethylenediamine-N,N'-disuccinic acid (EDDS), methylglycinediacetic acid (MGDA), L-glutamic acid N,N-diacetic acid (GLDA), 1,2-bis(o-aminophenoxy)ethane-N,N,N',N'-tetraacetic acid (BAPTA), and ethylene glycol tetraacetic acid (EGTA), with ethylenediaminetetraacetic acid disodium magnesium salt tetrahydrate ($Na_2MgEDTA$) being preferred.

The plurality of microwells can be sealed to prevent the composition from exiting the plurality of microwells. In some instances, the plurality of microwells is sealed with a plastic film or a foil. The hardness and/or magnesium ion assay kit can also include a spectrophotometer capable of measuring ultra violet and visible wavelengths.

In some instances, the hardness and/or magnesium ion assay kit contains a microwell plate with microwells that contain a lyophilized composition such that when an analyte composition is added to the lyophilized composition a solution forms having an absorbance at a detectable wavelength in response to the hardness comprised in the analyte composition and the microwell plate contains microwells that contain a lyophilized composition such that when an analyte composition is added to the lyophilized composition a solution forms having an absorbance at a detectable wavelength in response to magnesium ion.

Also disclosed are methods to use the hardness and/or magnesium ion assay kit of the present invention to determine the hardness and/or magnesium concentration of an analyte composition or a plurality of analyte compositions. The method can include a) obtaining any one of the hardness and/or magnesium ion assay kits described throughout this Specification; b) obtaining an analyte composition; c) adding substantially the same volume of the analyte composition to each of the plurality of microwells of the microwell plate to form solutions from the analyte composition and the lyophilized titrate compositions in each of the plurality of microwells; and d) measuring the absorbance value for each solution in each of the plurality of microwells at a wavelength and determining the hardness and/or magnesium ion concentration of the analyte composition based on the measured absorbance values in response to the hardness of and/or magnesium ion comprised in the analyte composition. The analyte can be obtained from a variety of sources such as a subsurface well, a hydrocarbon subsurface, a water well in a subsurface hydrocarbon formation, a wastewater reservoir or tank. In some instances, the analyte composition is obtained from a hydrocarbon drilling or fracking process. In some instances, a plurality of solutions having the same analyte is obtained, and each analyte composition is obtained from a different well of a plurality of subsurface wells or a plurality of different wastewater units.

The hardness and/or magnesium ion assay kits described throughout the specification can be made by a) obtaining a microwell plate; b) obtaining a lyophilized composition including an indicator, a buffer, and one or more excipients; wherein a plurality of microwells of the microwell plate contain the lyophilized composition such that when an analyte composition is added to the lyophilized composition in each microwell of the plurality of microwells a solution forms having an absorbance at a known wavelength in response to hardness of and/or magnesium ion comprised in the analyte composition. For the lyophilized composition in a hardness assay kit, the lyophilized composition further includes a metal complexation ligand. In some instances, the lyophilized composition can be obtained by providing an aqueous solution of the composition to one or more microwells of the microwell plate and subjecting the microwell plate to lyophilizing conditions sufficient to remove the water from the aqueous solution and form a powder. The plurality of microwells can be sealed with a plastic film or a foil to prevent the composition from exiting the plurality of microwells.

The term "acidic solution" or "acid compound" refers to a solution that has a concentration of hydrogen ions greater than the concentration of hydroxide ion ($[H+]>[OH^-]$).

The terms "basic solution" or "alkaline solution" refers to a solution that has a concentration of hydrogen ions less than the concentration of hydroxide ion ($[H+]<[OH^-]$).

The term "pH" refers to the measurement of the concentration of hydrogen ions in water or other media. pH is generally expressed as a log scale based on 10 where $pH=-\log[H+]$.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The hardness and/or magnesium ion assay kits and the methods of using and making the hardness and/or magnesium ion assay kits of the present invention can "comprise," "consist essentially of," or "consist of" particular ingredients, components, compositions, etc. disclosed throughout the specification. With respect to the transitional phase "consisting essentially of," in one non-limiting aspect, a basic and novel characteristic of the kits of the present invention is the ability to determine the hardness and/or magnesium concentration of an aqueous solution using spectrometric analysis.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description.

DETAILED DESCRIPTION OF THE INVENTION

Figure 1A:
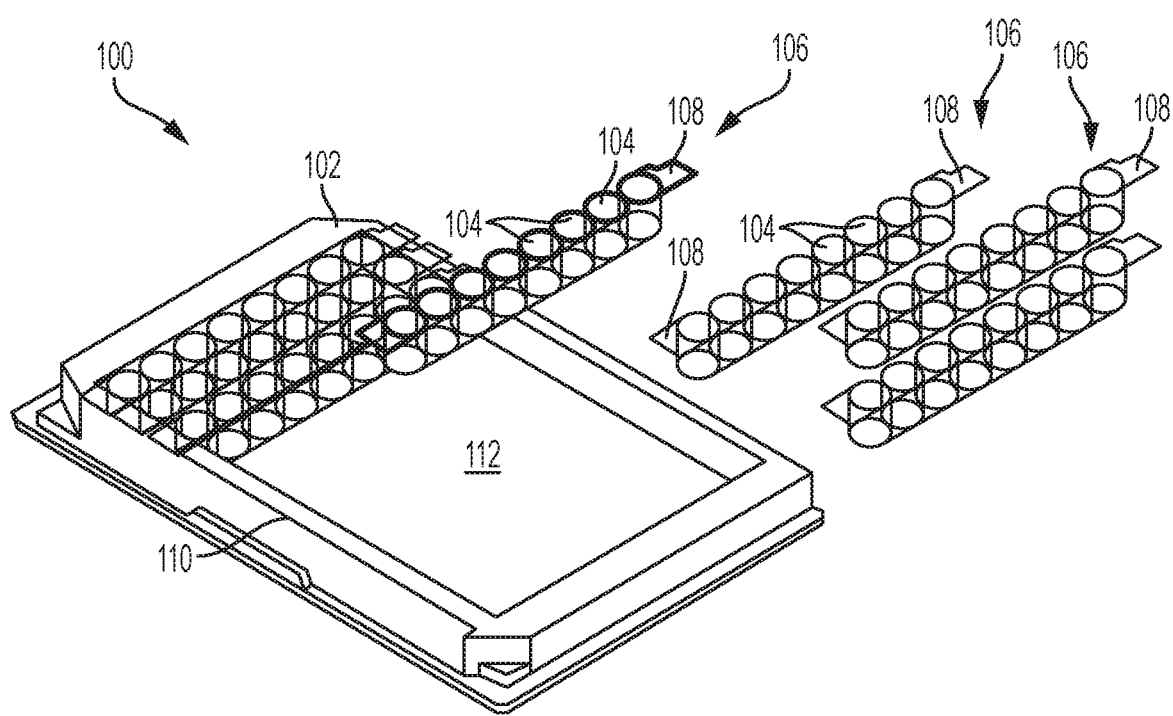
FIGS. 1A-1C are schematics of a hardness and/or magnesium ion assay kits of the present invention.

Conventional technologies used to determine the hardness and/or magnesium concentration of a solution involve visual titration methods that are time-consuming and often inaccurate. Many time, manual visual titrations result in error resulting from the analyst overshooting the endpoint due to adding too much titrant or misjudging the color change at the endpoint. A discovery has been made that avoids overshooting the endpoint, eliminating the need for a visual titration, and the use of EDTA. The discovery lies in the use of a lyophilized composition sample in a microwell plate. In some instances lyophilized composition for a hardness assay and a magnesium ion assay are contained in the same microwell plate. The composition can include an indicator, a buffer, and one or more excipients, wherein the composition has an absorbance at a detectable wavelength in response to the hardness of and/or magnesium ion comprised in the solution. For a lyophilized composition used in determining hardness, the lyophilized composition further includes a metal complexation ligand. In some instances, each microwell plate has at least two microwells having the same amount of composition. The analyte composition can be added to the lyophylized composition to form a solution and the hardness and/or magnesium concentration of the solution is determined by measuring the absorbance value for each solution in each of the plurality of wells at determining the hardness and/or magnesium concentration of the analyte composition based on the measured absorbance values on a calibration curve. For the hardness assay, the calcium and magnesium of the analyte form a metal-ligand-indicator complex having an absorbance that is different than the absorbance of the indicator alone. For the magnesium ion assay, the magnesium in the analyte complexes with the indicator to produce a metal complex having an absorbance that is different than the absorbance of the indicator alone. The amount of the colored complex formed is proportional to the amount of calcium and/or magnesium present in the sample. By developing calibration curves, the total hardness and/or magnesium concentration can be determined quantitatively.

These and other non-limiting aspects of the present invention are discussed in further detail in the following sections.

A. Composition

The composition can be made by preparing an aqueous solution of reagent solution and then subjecting the solution to lyophilizing conditions to remove the water and produce a powder. An aqueous solution of an indicator, a buffer, and one or more excipient can be prepared. For a hardness assay, a metal complexation ligand can also be prepared. The indicator can be one or more of a calcium and/or magnesium indicator including 3-hydroxy-4-(2-hydroxy-5-methylphenylazo)naphthalene-1-sulfonic acid (Calmagite), triethanol ammonium 3-hydroxy-4-(2-hydroxy-5-methylphenylazo) naphthalene-1-sulfonate (Calmagite triethanolammonium salt), 3-hydroxy-4-[(1-hydroxy-2-naphthyl)azo]naphthalene-1-sulphonate, sodium 3-hydroxy-4-[(1-hydroxy-2-naphthyl)azo]naphthalene-1-sulphonate (ERICHROME® Blue Black B), 2-hydroxy-1-(1-hydroxy-2-naphthylazo)-6-nitronaphthalene-4-sulfonic acid, sodium 2-hydroxy-1-(1-hydroxy-2-naphthylazo)-6-nitronaphthalene-4-sulfonic acid (ERICHROME® Black T), sodium 4-hydroxy-3-[2-hydroxy-3-(2,4-dimethylphenylaminocarbonyl)-1-naphthylazobenzenesulfonate (Magonsulfonate), 4-(4-nitrophenylazo)-1-naphthol (Magneson II). The buffer can be one or more buffering compound including N-cyclohexyl-3-aminopropanesulfonic acid (CAPS), camphor sulfonic acid (CSA), p-toluenesulfonic acid (PTSA), 1,4-piperazineethanesulfonic acid (PIPES), 4-(2-hydroxyethyl)-1-piperazineethanesulfonic acid (HEPES), 3-(N-morpholino)propanesulfonic acid (MOPS), and 2-(N-morpholino)ethanesulfonic acid (MES). For a hardness assay, the metal complexation ligand can be one or more of ethylenediaminetetraacetic acid disodium magnesium salt tetrahydrate (Na2MgEDTA), ethylenediaminetetraacetic acid (EDTA), iminodisuccinic acid (IDS), polyaspartic acid, ethylenediamine-N,N'-disuccinic acid (EDDS), methyl glycine diacetic acid (MGDA), L-glutamic acid N,N-diacetic acid (GLDA), 1,2-bis(o-aminophenoxy)ethane-N,N,N',N'-tetraacetic acid (BAPTA), and ethylene glycol tetraacetic acid (EGTA). For either and/or a combination assay, Suitable excipients of the composition include, but are not limited to, binders, diluents, disintegrants, detergents, surfactants, lubricants, glidants, carriers, and the like. A variety of materials may be used as fillers or diluents. The term "binder" in certain aspects refers to a substance that improves compression and promotes association between individual particles after compression. Binders can be used, for example, for dry granulation and direct compression, or dissolved in water or a solvent for use in wet granulation. Common binders include saccharides, gelatins, pregelatinized starches, microcrystalline cellulose, hydroxypropylcellulose and cellulose ethers, as well as polyvinylpyrrolidone (PVP). Suitable diluents or fillers include, but are not limited to, sucrose, dextrose, sorbitol, starch, cellulose (e.g. microcrystalline cellulose; Avicel®), dihydrated or anhydrous dibasic calcium phosphate, calcium carbonate, calcium sulfate, and others as known in the art. Suitable surfactants or detergents include nonionic surfactants, for example polyoxyethylene glycol alkyl ethers such as octaethylene glycol monododecyl ether and pentaethylene glycol monododecyl ether, polyoxypropylene glycol alkyl ethers, glucoside alkyl ethers, such as decyl glucoside, lauryl glucoside, and octyl glucoside, polyoxyethylene glycol octylphenyl ethers, such as TRITON™ X-45, X-114, X-100, and X-102, polyoxyethylene glycol alkylphenyl ethers, such as nonoxynol-4, -9, -14, -15, 18, -30, and -50, glycerol alkyl esters, such as glyceryl laurate, polyoxyethylene glycol sorbitan alkyl esters, sorbitan alkyl esters, cocamide MEA, cocamide DEA, dodecyldimethylamine oxide, and block copolymers of polyethylene glycol, such as polyethylene-glycol (PEG) 300, 400, 1000, 1540, 4000 and 8000. TRITON™ available from The Dow Chemical Company (Midland, Mich., USA) is 1,1,3,3-tetramethylbutyl) phenyl-polyethylene glycol having repeating ethylene glycol units equal to about 5 (1,1,3,3-tetramethylbutyl)phenyl-pentaethylene glycol, X-45), equal to about 7 or 8 (1,1,3,3-tetramethylbutyl)phenyl-hepta/octaethylene glycol, X-114), equal to about 9 or 10 (1,1,3,3-tetramethylbutyl)phenyl-nona/decaethylene glycol, X-100), or equal to about 12 (1,1,3,3-tetramethylbutyl)phenyl-dodecaethylene glycol, X-102). The excipients in the present embodiments can include, for example, one or more of a polyethylene glycol, a 1,1,3,3-tetramethylbutyl)phenyl-polyethylene glycol, (2-hydroxylpropyl)-β-cyclodextrin, glycine, cellulose, citrate, lactose, mannitol, xylitol, sucrose, trehalose, and polyvinylpyrrolidone.

For a hardness assay, the composition in solution can be diluted and filtered to form an aqueous reagent solution having a composition of from about 0.05 to 0.5 mM indicator, preferable 0.1 mM to about 0.3 mM indicator, from about 0.1 mM to about 1.0 mM metal complexation ligand, preferably from about 0.5 nM to about 0.7 mM metal complexation ligand, from about 100 to about 200 mM of buffer, preferably from about 130 mM to about 170 mM buffer, and from about 0.01% to about 10% excipients. The amounts of indicator, metal complexation ligand, buffer, and excipient or excipients can be determined based on the stoichiometric values of the aqueous reagent solution. In some instances, the aqueous reagent solution consists of 0.2 mM 3-hydroxy-4-(2-hydroxy-5-methylphenylazo)naphthalene-1-sulfonic acid (Calmagite), 0.6 mM ethylenediaminetetraacetic acid disodium magnesium salt tetrahydrate (Na2MgEDTA), 150 mM of N-cyclohexyl-3-aminopropanesulfonic acid (CAPS), 6% wt/wt of PEG 4000, and 0.01% wt/wt of TRITON™ X-100. Base (for example, sodium hydroxide) can be added to the solution to raise the pH to a value of from about 9 to about 11, preferably 9.8.

For the magnesium ion assay, the composition in solution can be diluted and filtered to form an aqueous reagent solution having a composition of from about 0.1 to 0.7 mM indicator, preferable 0.3 mM to about 0.5 mM indicator, from about 100 to about 200 mM of buffer, preferably from about 130 mM to about 170 mM buffer, and from about 0.01% to about 10% excipients. The amounts of magnesium indicator, buffer, and excipient or excipients can be determined based on the stoichiometric values of the aqueous reagent solution. In some instances, the aqueous reagent solution consists of 0.4 mM 3-hydroxy-4-(2-hydroxy-5-methylphenylazo)naphthalene-1-sulfonic acid (Calmagite), 150 mM of N-cyclohexyl-3-aminopropanesulfonic acid (CAPS), 6% wt/wt of PEG 4000, and 0.01% wt/wt of TRITON™ X-100. Base (for example, sodium hydroxide)

can be added to the solution to raise the pH to a value of from about 10 to about 12, preferably 10.2, or most preferably 11.7.

The reagent solution can be lyophilized and then specific amounts of the resulting powder can be added to each microwell of a microwell plate. In a preferred instance, a known volume of reagent solution is added to the microwells of the microwell plate and the microwell plate subjected to lyophilizing conditions. Lyophilizing conditions include −60° C. to −40° C., or −45° C. at 100 mtorr. For example, a 96-microwell plate can be filled with 100 microliters of aqueous reagent composition. In some instances, a microwell plate can contain microwells containing a lyophilized powder for a hardness assay and microwells containing a lyophilized powder for a magnesium ion assay.

B. Hardness and/or Magnesium Ion Assay Kit

Figure 1B:
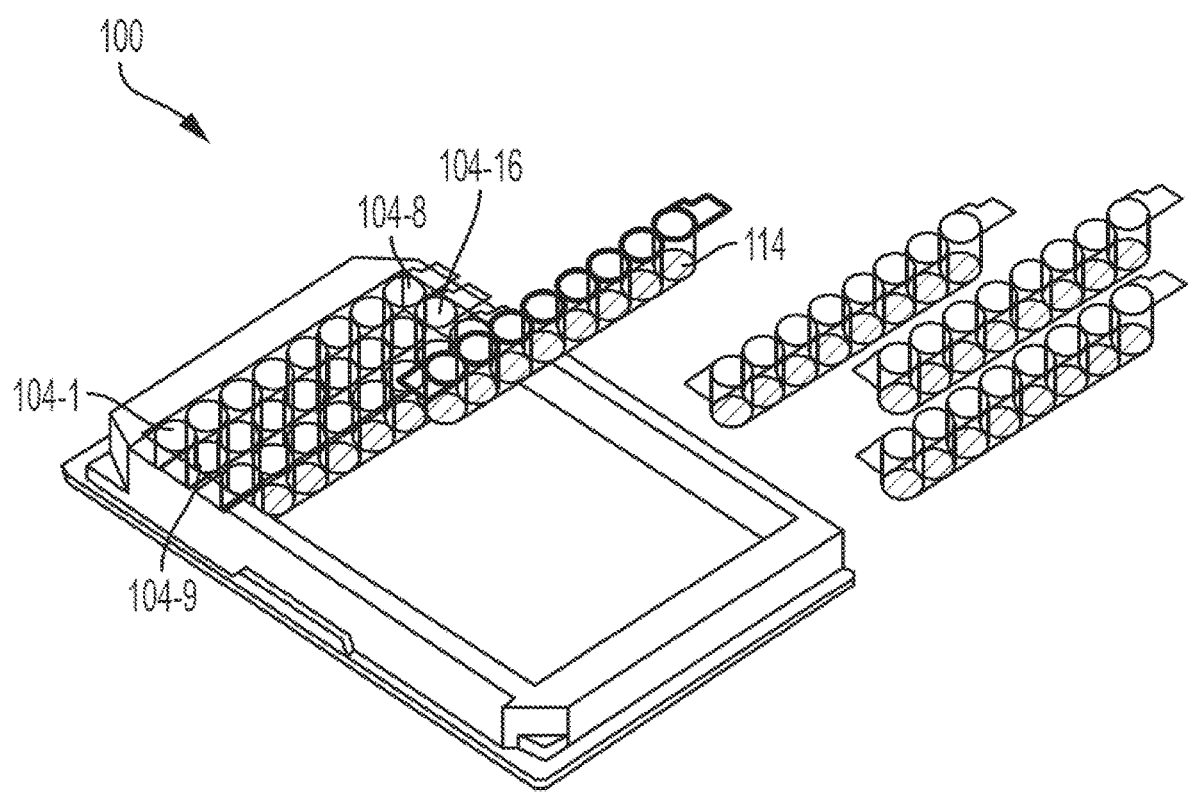
Figure 1C:
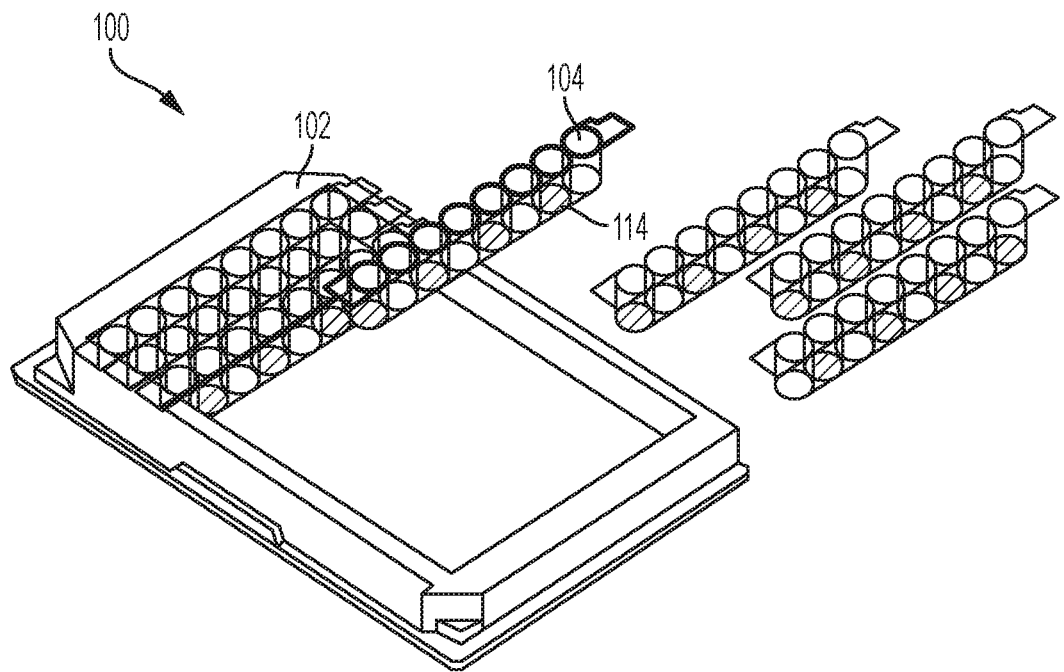

FIGS. 1A-1C depict schematics of embodiments of hardness and/or magnesium ion assay system 100. The hardness and/or magnesium ion assay system or kit includes microwell plate 102 having a plurality of microwells 104. The plurality of microwells 104 can be assembled in the removable holders 106. Holders 106 may include members 108 that position on top of the side wall 110. Holders 106 may rest on, or suspended above, bottom wall 112 of the microwell plate 102. As shown, holder 106 includes eight (8) microwells 104, however, it should be understood that the number of microwells can be adjusted to the size of the microwell plate 102. For example, the number of the microwells 104 can be 2, 3, 4, 5, 6, 7, 8, 9, 10, 11, 12, 13, 14, 15, 16, 17, 18, 19, 20, etc. As shown in FIG. 1A, the microwell plate 102 does not include any composition. FIG. 1B depicts all of the microwells having composition 114 and FIG. 1C depicts some of the microwells having composition 114. The microwells 104 can hold a volume of 20, 50, 300, 500 microliters, preferably 300 microliters or 400 microliters. The microwell plate 102, microwells 104, holders 106, can be made of any chemical resistant material. Non-limiting examples of materials include polymers, copolymers of polymers, polystyrene, polypropylene, cyclo-olefins and the like. The holders 106 may be polymeric or plastic tape with the microwells 104 embossed on the tape. Microwell plates are commercially available from Thermo Fisher Scientific (Waltham, Mass., USA).

As shown in FIG. 1B, the microwells 104 can be filled with the same amount of lyophilized composition. In other embodiments, the microwells 104 in each holder 106 can have the same amount of composition, but a total amount of composition in the holders 106 can be different. For example, microwells 104-1 to 104-8 can have a different amount of composition than microwells 104-9 to 104-16. It should be understood, that configuration of the amount composition in the microwells can be any chosen configuration that correlates to a calibration curve. In some instances, the microwells 104 are filled with a known amount of an aqueous solution of composition and then microwell plate is positioned in a lyophilizing unit and lyophilized under conditions sufficient to remove the water from the solution. The microwells 104, microwell holders 106, and/or the microwell plate can be sealed with a known sealing agent (for example, plastic film or foil) to allow the microwell plate 102 or the microwell holders 106 to stored or transported. In some embodiments, the hardness and/or magnesium assay system includes a spectrophotometer that is capable of measuring the absorbance of the chosen colorimetric dye and/or a calibration curve. The calibration curve depicts the amount of hardness and/or magnesium ion versus absorbance value. In some instances, a calibration curve is provided for each holder 106.

In yet another embodiment of the present invention, the hardness assay kit can be combined with the magnesium assay kit. Such an embodiment can be practiced by including both kits in a single microwell plate. By way of example, the lyophilized hardness assay composition can occupy a plurality of microwells, and the lyophilized magnesium assay can occupy a plurality of microwells in the same microwell plate. In one particular embodiment, and referring to FIG. 1B, microwells 104-1 to 104-8 can include the same or different amounts of lyophilized hardness composition. Microwells 104-9 to 104-16 can include the same or different amounts of the lyophilized magnesium composition.

C. Method of Determining Hardness and/or Magnesium Concentration

Figure 2:
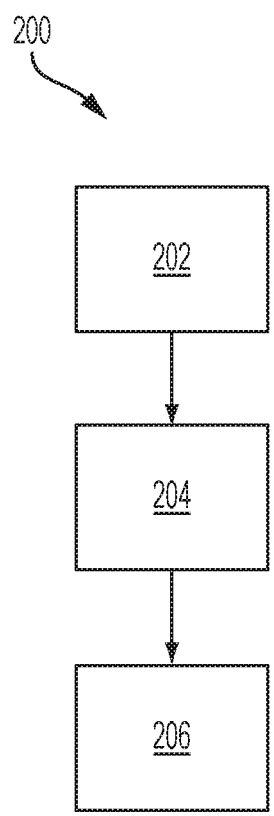
FIG. 2 is a flow chart depicting a method of determining the hardness and/or magnesium concentration of a water body.

The hardness and/or magnesium ion assay system and kit described throughout the specification can be used to determine the hardness and/or magnesium concentration of a solution. The solution can be a sample from a water body such as a subsurface water well in a hydrocarbon formation, a wastewater storage unit, a wastewater reservoir, a lake, a river, a canal or the like. Referring to FIG. 2, a flow chart for determining hardness and/or magnesium concentration is depicted. In method 200, the microwell plate 102 containing the lyophilized composition 114 is obtained in step 202. In step 204, a known amount of analyte composition (for example 300 microliters) is added to the lyophilized composition 114 reagents in the microwells 104 using a delivery apparatus (for example, multichannel pipette). In step 206, after solids in the plate have fully dissolved, the microwell plate 102 is placed in a spectrophotometer (for example, a plate reader) and the absorbance at the known wavelength (for example 450 nm) for each microwell is measured. The hardness and/or magnesium concentration is determined by referring to a calibration curve and selecting the hardness and/or magnesium concentration that correlates to the absorbance value.

The system 100 can be automated to acquire data. The acquired data can be transmitted to one or more computer systems. The computer systems can include components such as CPUs or applications with an associated machine readable medium or article which may store an instruction or a set of instructions that, if executed by a machine, may cause the machine to perform a method and/or operations in accordance with the methods of the present invention. For example, the microwell plate 102 can be put in a plate reader and the spectrophotometer can automatically measure the absorbance of each sample. The measured absorbance can be stored in a computer system in the spectrophotometer and/or transmitted to another computer system. Either computer may be capable of processing the absorbance and displaying or printing a hardness and/or magnesium ion value for a series of analytes. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, and the like. The instructions may be implemented using any suitable high-level, low-level, object-oriented, visual, compiled and/or interpreted programming language, such as C, C++, Java, BASIC, Perl, Matlab, Pascal, Visual BASIC, assembly language, machine code, and so forth. The computer system may further include a display device such as monitor, an alphanumeric input device such as keyboard, and a directional input device such as mouse.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Hardness Assay Kit

Composition—

TABLE 1

|  | for 1 L | for 2 L | for 5 L | for 10 L |
| --- | --- | --- | --- | --- |
| Calmagite | 72 mg | 144 mg | 360 mg | 720 mg |
| Na$_2$MgEDTA | 0.26 g | 0.52 g | 1.3 g | 2.6 g |
| CAPS (free) | 33.2 g | 66.4 g | 166 g | 332 g |
| PEG 4000 (flakes) | 60 g | 120 g | 300 g | 600 g |
| TRITON ™ X-100 (10% solution) | 1 mL | 2 mL | 5 mL | 10 mL |

The reagents listed in Table 1 were combined in distilled water in and diluted to approximately 75% of the desired batch size. The pH was slowly adjusted to a pH of 10.2 using concentrated (3-30%) sodium hydroxide prepared from ACS reagent grade sodium hydroxide and distilled water. Distilled water was added to increase the volume of the solution to approximately 95% of the batch size, the pH was monitored, and then the solution was transferred to an appropriately sized volumetric flask. The solution container was rinsed with small washes of distilled water and these rinses were transfer to the volumetric flask. The solution was then diluted to the desired volume (mark on the volumetric flask), and then filtered into an appropriate sized, clean media bottle using a bottle top or vacuum capsule filter, 0.22 microns.

The solution (100 µL) was added to microwells of a microwell plate. The aqueous composition was lyophilizing to remove the water and a lyophilized sample in the microwell plate was obtained. Plates were first frozen at −55° C. followed by primary drying at −45° C. and 100 mtorr vacuum until dry.

Figure 3:
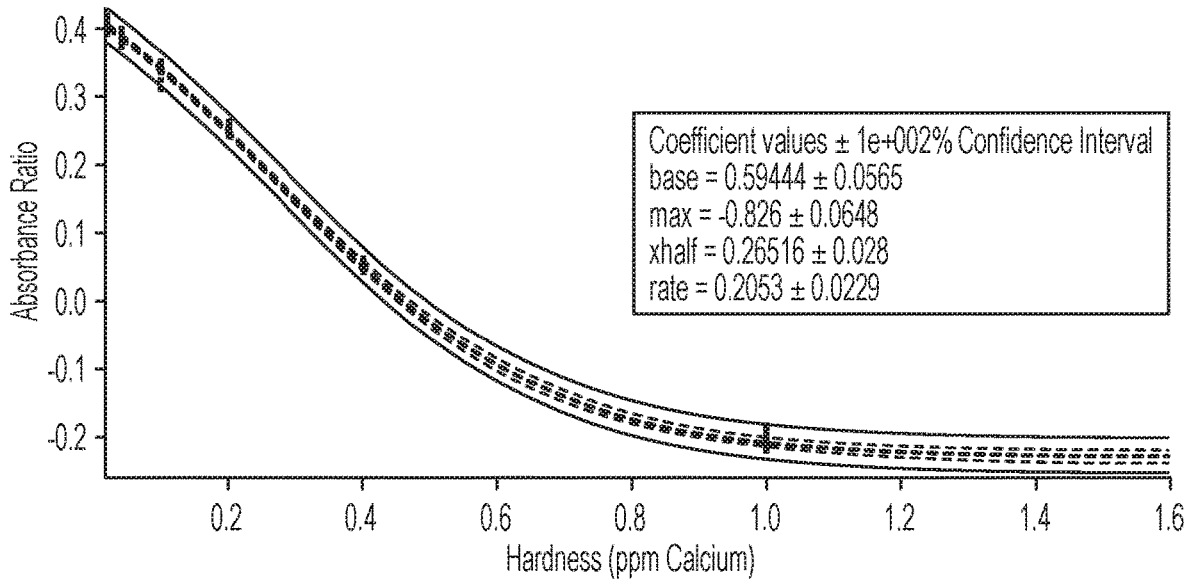
FIG. 3 is a graph of hardness (calcium ppm) versus absorbance.

Calibration Curve—A calibration curve was prepared by diluting a calcium standard (1000 mg/L Ca$^{2+}$ in 0.1% nitric acid, Sigma-Aldrich®) to the concentrations in Table 2, then filling a freeze-dried plate of a 100 microliter fill of the composition with 300 microliters of sample. The data was then fit with a second order polynomial as shown in FIG. 3.

TABLE 2

| Ca2+ (mg/L) | Absorbance | STDEV (OD) | STDEV (mg/L) | % RSD (OD) |
| --- | --- | --- | --- | --- |
| 0 | 0.233 | 0.003 | 0.013 | 1.49 |
| 0.0619 | 0.258 | 0.005 | 0.013 | 1.95 |
| 0.124 | 0.285 | 0.004 | 0.012 | 1.56 |
| 0.248 | 0.325 | 0.005 | 0.014 | 1.44 |
| 0.495 | 0.401 | 0.004 | 0.010 | 0.88 |
| 0.990 | 0.562 | 0.006 | 0.021 | 1.05 |
| 1.981 | 0.782 | 0.011 | 0.065 | 1.44 |
| 3.095 | 0.897 | 0.004 | 0.034 | 0.50 |

The lyophilized sample, the microwell plate and, optionally, a calibration curve or table constituted the hardness assay kit.

Example 2

Determination of Hardness in a Water Body

Hardness Assay—Analyte compositions (300 microliters) containing an unknown amount of hardness were added to 7 microwells of the 96-microwell plate prepared in Example 1. After dissolution of the lyophilized sample, the microwell plate was positioned in a plate reader and the absorbance value of the plate was determined.

The absorbance value was plotted against the calibration curve. The absorbances are plotted as a function of the absorbances determined from the following equation:

$$(620 \text{ nm}/560 \text{ nm})-(520 \text{ nm}/560 \text{ nm}).$$

Table 3 shows how the current hardness assay compares to two different third party labs running ICP-MS (Lab 1) and ICP-OES (Lab 2). Each of the samples is from an oil field water well.

TABLE 3

| Sample ID | Lab 1 | Lab 2 | Water Lens |
| --- | --- | --- | --- |
| #011 | 6,836 | 5,864 | 6,705 |
| #012 | 20,028 | 17,201 | 18,342 |
| #014 | 8,529 | 7,437 | 9,450 |
| #018 | 262 | 254 | 289 |
| #034 | 950 | 861 | 921 |
| #035 | 999 | 898 | 935 |

Example 3

Magnesium Assay Kit

Composition

TABLE 4

|  | for 1 L | for 2 L | for 5 L | for 10 L |
| --- | --- | --- | --- | --- |
| Calmagite | 144 mg | 288 mg | 720 mg | 1440 mg |
| CAPS (free) | 33.2 g | 66.4 g | 166 g | 332 g |
| PEG 4000 (flakes) | 60 g | 120 g | 300 g | 600 g |
| TRITON ™ X-100 (10% solution) | 1 mL | 2 mL | 5 mL | 10 mL |

The reagents in Table 4 were combined for a selected volume with distilled water and diluted to approximately 75% of the desired batch size with agitation. pH and temperature probes (for ATC) of a calibrated pH meter were inserted into the solution. The pH was slowly adjusted to a pH of 10.2 using concentrated (3-30%) sodium hydroxide prepared from ACS reagent grade sodium hydroxide and distilled water. The solution was diluted up to approximately 95% of the batch size with distilled water, the pH monitored, and then transferred to an appropriately sized volumetric flask. The solution container was washed several times with small washes of distilled water and transferred to the flask. Sufficient distilled water was added to bring the total volume of solution to a desired amount. The solution was filtered into an appropriate sized, clean media bottle using a bottle top or vacuum capsule filter, 0.22 microns.

The solution (100 fL) was added to microwells of a 96 microwell plate. The aqueous composition was lyophilizing to remove water to obtain the lyophilized sample in the microwell plate. Plates were first frozen at −55° C. followed by primary drying at −45° C. and 100 mtorr vacuum until dry.

The lyophilized composition, the microwell plate and, optionally, a calibration curve or table constituted the magnesium assay kit.

Example 4

Determination of Magnesium in a Water Body

Magnesium Assay—Analyte compositions (300 microliters) containing an unknown amount of magnesium were added to 7 microwells of the 96-microwell plate prepared in Example 3. After dissolution of the lyophilized composition, the microwell plate was positioned in a plate reader and the absorbance value of the plate was determined.

Figure 4:
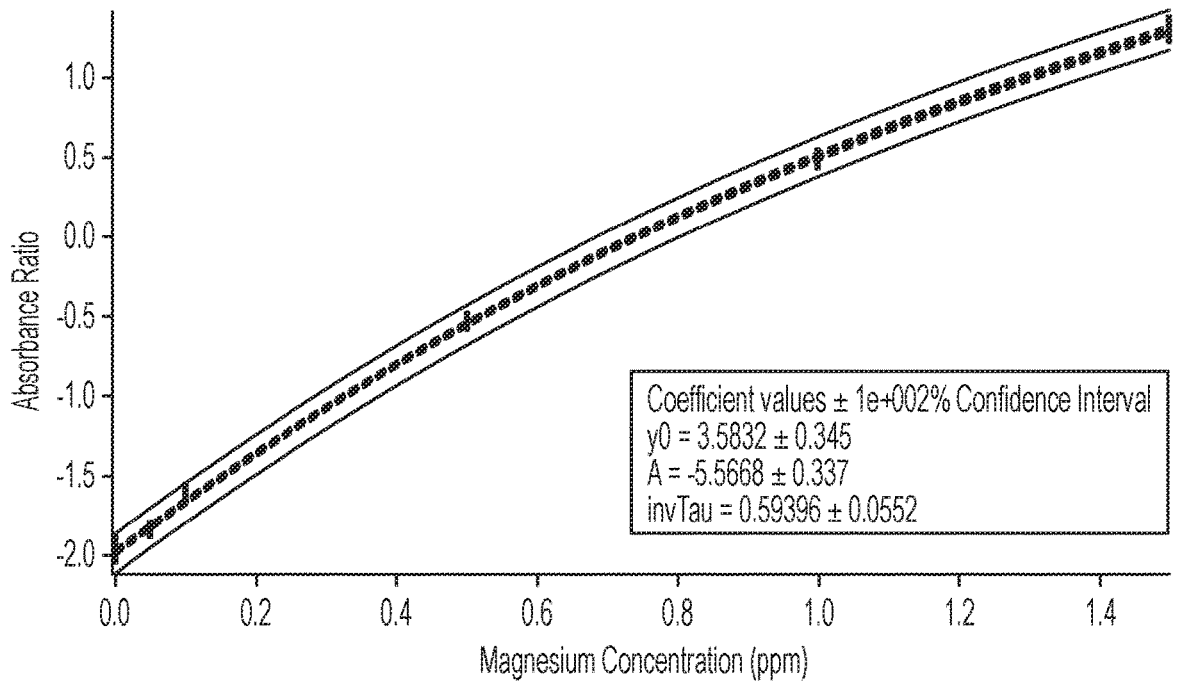
FIG. 4 is a graph of magnesium concentration (ppm) versus absorbance.

The absorbance value was plotted against the calibration curve. FIG. 4 is a plot of the calibration curve. Table 5 shows how the current magnesium assay compares to two different third party labs running ICP-MS (Lab 1) and ICP-OES (Lab 2). Each samples is from an oil field water well.

TABLE 5

| Sample ID | Lab 1 | Lab 2 | Water Lens |
|---|---|---|---|
| #011 | 307 | 230 | 309 |
| #012 | 656 | 608 | 756 |
| #014 | 391 | 301 | 488 |
| #018 | 27 | 25 | 26 |
| #034 | 142 | 126 | 149 |
| #035 | 45 | 40 | 47 |

As discussed throughout this specification, an additional embodiment that is contemplated is the combination of the hardness assay kit with the magnesium assay kit. Such an embodiment can be practiced by including both kits in a single microwell plate. By way of example, the lyophilized hardness assay composition can occupy a plurality of microwells, and the lyophilized magnesium assay can occupy a plurality of microwells in the same microwell plate. In one particular embodiment, and referring to FIG. 1B, microwells 104-1 to 104-8 can include the same or different amounts of lyophilized hardness composition. Microwells 104-9 to 104-16 can include the same or different amounts of the lyophilized magnesium composition.

The invention claimed is:

1. A method of determining the hardness and/or magnesium ion concentration of an analyte composition, the method comprising:
    a) obtaining a hardness and/or magnesium assay kit comprising:
        (i) a microwell plate; and
        (ii) a lyophilized composition comprising an indicator, a buffer, and one or more excipients,
        wherein a plurality of microwells of the microwell plate contain the lyophilized composition such that when an analyte composition is added to the lyophilized composition in each microwell of the plurality of microwells a solution forms having an absorbance at a detectable wavelength in response to the hardness and/or magnesium ion comprised in the analyte composition;
    b) obtaining an analyte composition;
    c) adding substantially the same volume of the analyte composition to each of the plurality of microwells of the microwell plate to form solutions from the analyte composition and the lyophilized composition in each of the plurality of microwells;
    d) measuring the absorbance value for each solution in each of the plurality of microwells at a wavelength and determining the hardness and/or magnesium ion concentration of the analyte composition based on the measured absorbance values,
    wherein the indicator comprises sodium 1-(1-hydroxy-4-methyl-2-phenylazo)-2-naphthol-4-sulfonic acid, and
    wherein the one or more excipients comprises polyethylene glycol 4000 and 1,1,3,3-tetramethylbutyl)phenyl-nona/decaethylene glycol.

2. The method of claim 1, wherein the indicator further comprises one or more of 3-hydroxy-4-(2-hydroxy-5-methylphenylazo)naphthalene-1-sulfonic acid, triethanol ammonium 3-hydroxy-4-(2-hydroxy-5-methylphenylazo)naphthalene-1-sulfonate, 3-hydroxy-4-[(1-hydroxy-2-naphthyl)azo]naphthalene-1-sulphonate, sodium 3-hydroxy-4-[(1-hydroxy-2-naphthyl)azo]naphthalene-1-sulphonate, 2-hydroxy-1-(1-hydroxy-2-naphthylazo)-6-nitronaphthalene-4-sulfonic acid, sodium 2-hydroxy-1-(1-hydroxy-2-naphthylazo)-6-nitronaphthalene-4-sulfonic acid, sodium 4-hydroxy-3-[2-hydroxy-3-(2,4-dimethylphenylaminocarbonyl)-1-naphthylazobenzenesulfonate, and 4-(4-nitrophenylazo)-1-naphthol.

3. The method of claim 1, wherein the lyophilized composition further comprises a metal complexation ligand.

4. The method of claim 3, wherein the metal complexation ligand comprises one of more of ethylenediaminetetraacetic acid disodium magnesium salt tetrahydrate, ethylenediaminetetraacetic acid, iminodisuccinic acid, polyaspartic acid, ethylenediamine-N,N'-disuccinic acid, methylglycinediacetic acid, N,N-diacetic acid-L-glutamic acid, 1,2-bis(o-aminophenoxy)ethane-N,N,N',N'-tetraacetic acid, and ethylene glycol tetraacetic acid.

5. The method of claim 3, wherein the metal complexation ligand is ethylenediaminetetraacetic acid disodium magnesium salt tetrahydrate.

6. The method of claim 1, wherein the buffer comprises one of more of N-cyclohexyl-3-aminopropanesulfonic acid, camphor sulfonic acid, p-toluenesulfonic acid, 1,4-piperazinediethanesulfonic acid, 4-(2-hydroxyethyl)-1-piperazineethanesulfonic acid, 2-(N-morpholino)ethanesulfonic acid, 3-(N-morpholino)propanesulfonic acid, and 2-(N-morpholino)ethanesulfonic acid.

7. The method of claim 1, wherein the buffer is N-cyclohexyl-3-aminopropanesulfonic acid.

8. The method of claim 1, wherein the one or more excipients further comprises one or more of a polyethylene glycol, a 1,1,3,3-tetramethylbutyl)phenyl-polyethylene glycol, (2-hydroxylpropyl)-β-cyclodextrin, glycine, cellulose, citrate, lactose, mannitol, xylitol, sucrose, trehalose and polyvinylpyrrolidone.

9. The method of claim 1, wherein the lyophilized composition is a powder.

10. The method of claim 9, wherein the powder is made by providing an aqueous solution of the composition to one or more containers and subjecting at least one of the containers to lyophilizing conditions sufficient to remove the water from the aqueous solution to form the powder.

11. The method of claim 10, wherein the one or more containers are microwells of a microwell plate.

12. The method of claim 11, wherein the powder composition for determining the hardness and the powder composition for determining magnesium content of a solution are both made in the same microwell plate.

13. The method of claim 1, wherein the analyte in is an aqueous composition obtained from a subsurface well.

14. The method of claim 1, wherein the analyte composition comprises a plurality of solutions having the same analyte, and each analyte composition is obtained from a different well of a plurality of subsurface wells.

15. The method of claim 1, wherein the analyte composition is obtained from a drilling process or fracking process.

16. The method of claim 1, wherein the analyte composition is obtained from a wastewater tank or reservoir.

17. A method of determining the hardness of an analyte composition, the method comprising:
   a) obtaining a hardness assay kit comprising:
      (i) a microwell plate; and
      (ii) a lyophilized composition comprising an indicator, a buffer, and one or more excipients,
      wherein a plurality of microwells of the microwell plate contain the lyophilized composition such that when an analyte composition is added to the lyophilized composition in each microwell of the plurality of microwells a solution forms having an absorbance at a detectable wavelength in response to the hardness of the analyte composition;
   b) obtaining an analyte composition;
   c) adding substantially the same volume of the analyte composition to each of the plurality of microwells of the microwell plate to form solutions from the analyte composition and the lyophilized composition in each of the plurality of microwells;
   d) measuring the absorbance value for each solution in each of the plurality of microwells at a wavelength and determining the hardness of the analyte composition based on the measured absorbance values,
   wherein the composition consists essentially of 3-hydroxy-4-(2-hydroxy-5-methylphenylazo)naphthalene-1-sulfonic acid, ethylenediaminetetraacetic acid disodium magnesium salt tetrahydrate, N-cyclohexyl-3-aminopropanesulfonic acid, polyethylene glycol 4000, and 1,1,3,3-tetramethylbutyl)phenyl-nona/decaethylene glycol.

18. A method of determining the magnesium ion concentration of an analyte composition, the method comprising:
   a) obtaining a magnesium assay kit comprising:
      (i) a microwell plate; and
      (ii) a lyophilized composition comprising an indicator, a buffer, and one or more excipients,
      wherein a plurality of microwells of the microwell plate contain the lyophilized composition such that when an analyte composition is added to the lyophilized composition in each microwell of the plurality of microwells a solution forms having an absorbance at a detectable wavelength in response to the magnesium ion concentration comprised in the analyte composition;
   b) obtaining an analyte composition;
   c) adding substantially the same volume of the analyte composition to each of the plurality of microwells of the microwell plate to form solutions from the analyte composition and the lyophilized composition in each of the plurality of microwells;
   d) measuring the absorbance value for each solution in each of the plurality of microwells at a wavelength and determining the magnesium ion concentration of the analyte composition based on the measured absorbance values,
   wherein the lyophilized composition consists essentially of 3-hydroxy-4-(2-hydroxy-5-methylphenylazo)naphthalene-1-sulfonic acid, N-cyclohexyl-3-aminopropanesulfonic acid, polyethylene glycol 4000, and 1,1,3,3-tetramethylbutyl)phenyl-nona/decaethylene glycol.

* * * * *